United States Patent
Sheremata et al.

(10) Patent No.: US 10,302,615 B2
(45) Date of Patent: May 28, 2019

(54) METHOD TO TUNE RADIO FREQUENCIES TO BREAK EMULSIONS

(71) Applicant: CONOCOPHILLIPS COMPANY, Houston, TX (US)

(72) Inventors: Jeff Michael Sheremata, Houston, TX (US); Peter Nelson Slater, Bartlesville, OK (US)

(73) Assignee: CONOCOPHILLIPS COMPANY, Houston, TX (US)

( * ) Notice: Subject to any disclaimer, the term of this patent is extended or adjusted under 35 U.S.C. 154(b) by 235 days.

(21) Appl. No.: 15/178,592

(22) Filed: Jun. 10, 2016

(65) Prior Publication Data

US 2016/0363574 A1  Dec. 15, 2016

Related U.S. Application Data

(60) Provisional application No. 62/174,195, filed on Jun. 11, 2015.

(51) Int. Cl.
*G01N 33/18* (2006.01)
*G01N 33/28* (2006.01)

(52) U.S. Cl.
CPC ............ *G01N 33/18* (2013.01); *G01N 33/28* (2013.01)

(58) Field of Classification Search
CPC ...... B01D 17/04; B01D 17/042; B01J 19/126; C10G 33/00; C10G 33/06; H05B 6/707; H05B 6/76; H05B 6/802; H05B 6/705; G01N 33/18; G01N 33/28
See application file for complete search history.

(56) References Cited

U.S. PATENT DOCUMENTS

| | | | | |
|---|---|---|---|---|
| 5,885,242 A | * | 3/1999 | Arick | A61F 11/00 128/207.18 |
| 5,914,014 A | * | 6/1999 | Kartchner | B01D 17/04 204/157.15 |
| 6,077,400 A | * | 6/2000 | Kartchner | B01D 17/04 204/157.15 |
| 6,086,830 A | * | 7/2000 | Kartchner | B01D 17/00 422/186 |
| 6,440,312 B1 | | 8/2002 | Kasevich | |
| 7,889,146 B2 | | 2/2011 | Halek et al. | |

OTHER PUBLICATIONS

Kovaleva et al. Destruction of Water-in-Oil Emulsions in Radio-Frequency and Microwave Electromagnetic Fields. Energy Fuels 25(8): 3731-3738, 2011.
Liu et al. Molecular Dynamics Simulation of Self-Aggregation of Asphaltenes at an Oil/Water Interface: Formation and Destruction of the Asphaltene Protective Film. Energy Fuels 29(2): 1233-1242, 2015 (Publication date (web): Jan. 19, 2015).
International Search Report and Written Opinion for related case, App. No. PCT/US2016/036818, dated Oct. 17, 2016.

* cited by examiner

*Primary Examiner* — Walter D. Griffin
*Assistant Examiner* — Cameron J Allen
(74) *Attorney, Agent, or Firm* — Conocophillips Company

(57) ABSTRACT

A method for determining an optimal radio frequency to break an emulsion comprises: analyzing an oil and water interface of an emulsion; defining the oil and water interface at a molecular level; simulating oscillation of molecules at the oil and water interface under different radio frequencies; and determining an optimal radio frequency to break the emulsion.

20 Claims, 1 Drawing Sheet

METHOD TO TUNE RADIO FREQUENCIES TO BREAK EMULSIONS

CROSS-REFERENCE TO RELATED APPLICATIONS

This application is a non-provisional application which claims benefit under 35 USC § 119(e) to U.S. Provisional Application Ser. No. 62/174,195 filed Jun. 11, 2015, entitled "METHOD TO TUNE RADIO FREQUENCIES TO BREAK EMULSIONS," which is incorporated herein in its entirety.

STATEMENT REGARDING FEDERALLY SPONSORED RESEARCH

None.

FIELD

This disclosure relates to methods to tune radio frequencies to disrupt emulsions, particularly to methods of determining optimal radio frequencies to break crude oil emulsions.

BACKGROUND

Emulsions in the oil and gas industry are common. Crude oil emulsions can form when water and oil come into contact with each other, particularly when there is sufficient mixing and when surfactants or emulsifiers are present. For both environmental and economic reasons, it is desirable to separate water from oil. The most common method of emulsion treatment is the application of heat and an appropriate chemical demulsifier to promote destabilization of emulsifying films around water droplets. However, chemical demulsifiers can present an economic burden. The demulsifiers can also contaminate water and cause water disposal problems. Thus, the industry is always receptive to environmentally friendlier and more cost effective methods to break emulsions.

SUMMARY

In an embodiment, a method of determining an optimal radio frequency to break an emulsion comprises: analyzing an oil and water interface of an emulsion; defining the oil and water interface at a molecular level; simulating oscillation of molecules at the oil and water interface under different radio frequencies; and determining an optimal radio frequency to break the emulsion.

In another embodiment, a method for determining an optimal radio frequency to break a water-in-oil emulsion comprises: isolating molecules at an oil and water interface of an emulsion; analyzing the isolated molecules to obtain chemical characterization data; creating a simulation cell to define the interface at a molecular level; selecting at least one molecule isolated from the oil and water interface for simulation; monitoring the rotations, translations, or a combination thereof of each of the selected molecules as a function of radio frequencies applied to the simulation cell; and determining an optimal radio frequency to break the emulsion.

An electromagnetic energy having the determined optimal radio frequency can then be applied to an emulsion to break the emulsion.

BRIEF DESCRIPTION OF THE DRAWINGS

The invention, together with further advantages thereof, may best be understood by reference to the following description taken in conjunction with the accompanying figures by way of example and not by way of limitation, in which.

DETAILED DESCRIPTION

Figure 1:
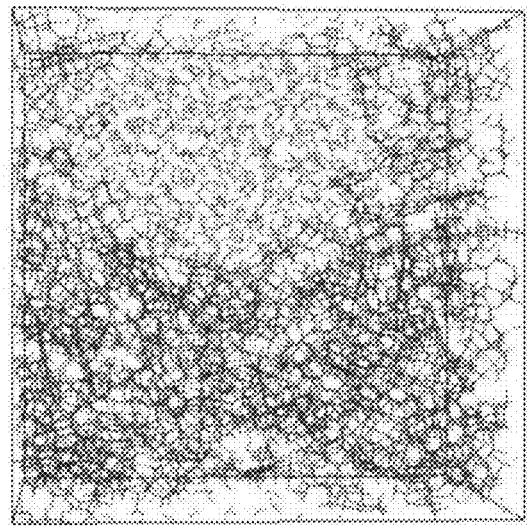
FIG. 1 is a view of an atomistic simulation cell of a crude oil brine emulsion.

Radio frequency heating is a promising technology to break emulsions in an environmentally friendly manner. However, radio frequencies have to be finely tuned. Otherwise, it will not effectively disrupt or break the emulsions.

Without wishing to be bound by theory, it is believed that molecular dipoles oscillate in the constantly varying electromagnetic field. Each oil molecule in the emulsion has a specific optimal frequency of oscillation. When the electric field oscillates at the optimal frequency, the molecule's motion is maximized. The motion and the heat it generates disrupt the interface and allow the emulsion to break.

The inventors hereof have developed a method of determining an optimal radio frequency to break emulsions. As used herein, "optimal radio frequency" refers to the radio frequency that is the most likely to trigger the largest impact on the molecules at the oil and water interface of an emulsion. An optimal radio frequency is not limited to a fixed value and can include a range of radio frequencies.

The method minimizes the costs that may otherwise be required to determine the effective ways to break an emulsion. It can be suitably used to determine the optimal radio frequency to break wide varieties of emulsions, including but are not limited to, production emulsions both on the surface and in the subsurface. In an embodiment, the emulsion is a water-in-crude oil emulsion, which contains about 1 to about 60 volume percent of water. As used herein, water refers to an aqueous phase and includes brines.

Emulsions can contain both a dispersed and a continuous phase, with the boundary between the phases called the "interface." While emulsions can include a large variety of constituents such as inorganic fine particles, apolar and polar resins, asphaltenes, naturally occurring and synthetic surfactants, the composition of the interface plays an important role in stabilizing the emulsions. Thus, an analysis of the composition at the interface can provide information for determining the optimal radio frequency to break the emulsions.

An analysis of the oil and water interface includes isolating molecules at the interface and charactering the isolated molecules. The isolation methods are known in the art and include extraction, distillation, chromatography, centrifugation, crystallization, filtration, flotation, and the like. The characterization methods are not limited and include nuclear magnetic resonance (NMR) spectroscopy, mass spectroscopy, elemental analysis, simulated distillation, and Fourier transform infrared spectroscopy. Other methods known in the art can also be used. The chemical characterization data includes structures, formulas, molecular mass of the isolated molecules, or molar percentages of the isolated molecules, or a combination comprising at least one of the foregoing. In an embodiment, the molecular structures for the isolated molecules are determined.

It is appreciated that not all the compounds at the interface have to be isolated because of the existence of equivalent features or functional groups. In an embodiment, the isolated compounds comprise asphaltenes and surfactants such as alkyl benzene sulfonates. Sodium dodecyl benzene sulfonate can be specifically mentioned. Known information about compounds that are typically present in the interface of a crude oil and water emulsion can also be used.

A model can then be created based on the obtained chemical characterization data to define the emulsion interface at a molecular level. When constructing the model, the possibility of local ordering such as stacking and orientation of the molecules can be taken into consideration. Tools such as MedeA®-amorphous builder from Materials Design® can be used to create a model such as a simulation cell. A review of an atomistic simulation cell of a crude oil brine emulsion is illustrated in FIG. 1.

Once the model has been created, oscillation simulation can be performed on the molecules at the oil and water interface under different radio frequencies. The molecules isolated from emulsion interface can include apolar resins or asphaltenes that do not contain heteroatoms such as oxygen, nitrogen, and sulfur. These apolar molecules have small or null dipoles. Accordingly, the dielectric field may not affect these molecules directly but through the motion of neighboring polar molecules. In an embodiment, a set of molecules are selected for oscillation simulation. The selected molecules are those that are more likely to respond to electric field. For example, the selected molecules have a high dipole or are polar.

Quantum mechanical simulation of dipole oscillation can be conducted for each of the selected molecules. During the simulation, an external radio frequency field is applied to the simulation cell to investigate the molecular motions, i.e., rotations and translations, as a function of radio frequencies. The external radio frequency can be about 500 kHz to about 500 MHz. In an embodiment, the simulation is conducted under an external electric radio frequency field at frequencies of about 0.5, 5, 10, 15, 20, 25, 50, 75, 100, 150, 200, 250, 300, 350, 400, 450 or even about 500 MHz. Other frequencies within the range of about 500 KHz to about 500 MHz can also be applied.

In the instance where the oil/water emulsion model is not homogeneous along the x, y, and z-axis, the electric field can be separately applied along the x, y, and z-axis and consequently compounded the average of the effect of the radio frequency electric field.

The electric field intensity is about 1.5 V $Å^{-1}$ to about 1.5×$10^{-4}$ V $Å^{-1}$, specifically about $10^{-1}$ V $Å^{-1}$ to about $10^{-3}$ V $Å^{-1}$. Without wishing to be bound by theory, it is believed that an electric field with an intensity of 1 V $Å^{-1}$ or more may lead to rather unrealistic molecule diffusion, i.e., the molecules are beyond the electric field point rupture. With an intensity of $10^{-4}$ $Å^{-1}$ or less, the effect on the mean square displacement is almost negligible and can be misled with statistical noise.

If desirable, the system can be pre-equilibrated without external electric field before applying the electric field with the desired frequency and intensity. The molecular mean square displacement and angular momentum can be sampled for as little as a few nanoseconds along an axis using tools such as MedaA®-LAMMPS available from Materials Design®. This simulation is performed similarly along the two other axes.

Figure 2:
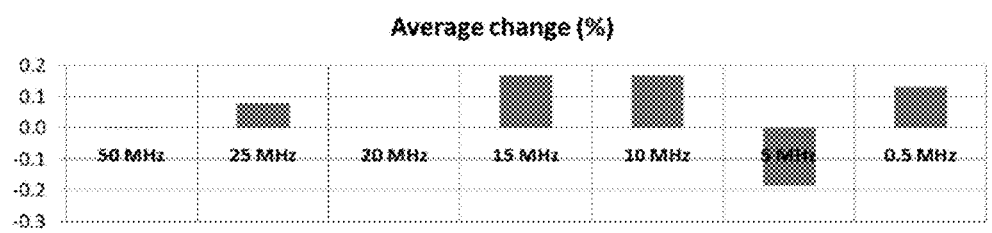
FIG. 2 shows the overall change on the molecular angular momentum in an exemplary crude oil brine emulsion as a function of the electric field frequency.
Figure 3:
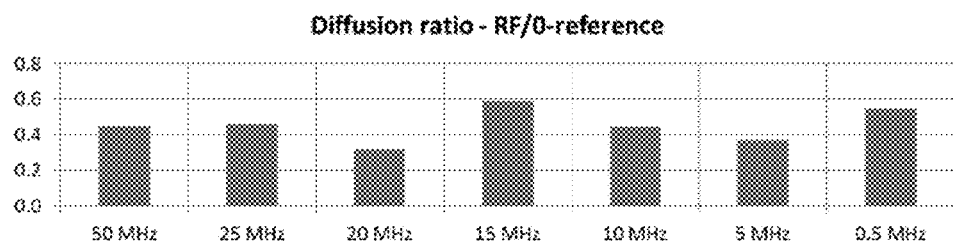
FIG. 3 shows the overall change on the molecular diffusion in an exemplary crude oil brine emulsion as a function of the electric field frequency.

The angular momentum and the mean square displacement on the selected molecules before and after the application of the electrical field can be compared. Once the variations of the angular momentum and the mean square displacement on each of the selected molecules have been determined, the averages of these values are calculated to determine an optimal radio frequency to break the emulsion. The overall change on the molecular angular momentum in an exemplary crude oil water emulsion as a function of the electric filed frequency is shown in FIG. 2. The overall change on the molecular diffusion in an exemplary crude oil water emulsion as a function of the electric field frequency is illustrated in FIG. 3. In FIG. 3, the diffusion change is expressed as the ratio of the diffusion in the presence and absence of external electric field. Based on the results from FIGS. 2 and 3, the optimal radio frequency to break the exemplary emulsion is about 10 to about 15 MHz.

The optimal radio frequency obtained from the method can be used in the field to break emulsions. It can also be used subsequently in a pilot/lab tests to minimize the expense. A correlation model may also be used to determine the optimal RF based on molecular descriptors. Once established the model could be used to calculate optimal RF based on molecular descriptors rather than actual simulations using values for specific molecular configurations.

All ranges disclosed herein are inclusive of the endpoints, and the endpoints are independently combinable with each other. "Or" means 'and/or." As used herein, "combination" is inclusive of blends, mixtures, alloys, reaction products, and the like. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. The modifier "about" used in connection with a quantity is inclusive of the stated value and has the meaning dictated by the context (e.g., it includes the degree of error associated with measurement of the particular quantity).

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A method for determining an optimal radio frequency to break an emulsion, the method comprising:
    analyzing an oil and water interface of an emulsion to obtain chemical characterization data;
    defining the oil and water interface at a molecular level based on the chemical characterization data;
    simulating oscillation of molecules at the oil and water interface under different radio frequencies;
    determining an optimal radio frequency to break the emulsion based on the oscillation of the molecules at the oil and water interface;
    generating, at a frequency generator, the optimal radio frequency; and
    applying the optimal radio frequency to the emulsion.

2. The method of claim 1, wherein analyzing the oil and water interface comprises separating molecules at the interface; and characterizing the separated molecules.

3. The method of claim 2, wherein the molecules are separated through one or more of the following methods:

extraction; distillation; chromatography; centrifugation; crystallization; filtration; or flotation.

4. The method of claim 2, wherein the separated molecules comprise at least one of asphaltenes and surfactants.

5. The method of claim 2, wherein the separated molecules are characterized by one or more of the following methods: nuclear magnetic resonance spectroscopy; mass spectroscopy; elemental analysis; simulated distillation; or Fourier transform infrared spectroscopy.

6. The method of claim 2, wherein characterizing the separated molecules comprises obtaining chemical characterization data comprising at least one of the following: chemical structures; chemical formula; molecular mass; or molar percent of the separated molecules in the interface.

7. The method of claim 1, wherein defining the oil and water interface at the molecular level comprises creating a simulation cell.

8. The method of claim 1, wherein the molecules at the oil and water interface are polar molecules isolated from the water and oil interface.

9. The method of claim 1, wherein simulating oscillation comprises monitoring the rotations and translations of the molecules at the oil and water interface as a function of radio frequencies.

10. The method of claim 9, wherein monitoring the rotations and translations of the molecules comprises determining an angular momentum or an mean square displacement of the molecules before and after a radio frequency is applied to a simulation cell.

11. The method of claim 1, wherein the radio frequencies are about 500 KHz to about 500 MHz, including about 0.5, 5, 10, 15, 20, 25, 50, 75, 100, 150, 200, 250, 300, 350, 400, 450, or 500 MHz.

12. The method of claim 1, wherein determining the optimal radio frequency comprises calculating averages of angular momentum variations or averages of mean square displacement variations before and after radio frequencies are applied.

13. The method of claim 1, wherein the emulsion is a water-in-crude oil emulsion.

14. The method of claim 1, wherein the generated optimal frequency is an electromagnetic energy.

15. The method of claim 7, wherein the defining the oil and water interface at the molecular level includes selecting at least one molecule isolated from the oil and water interface for simulation.

16. A method for determining an optimal radio frequency to break a water-in-oil emulsion, the method comprising:
   isolating molecules at an oil and water interface of an emulsion;
   analyzing the isolated molecules to obtain chemical characterization data;
   creating a simulation cell to define the interface at a molecular level;
   selecting one or more of the molecules isolated from the oil and water interface for simulation;
   monitoring the rotations, translations, or a combination thereof of each of the one or more of the molecules as a function of radio frequencies applied to the simulation cell;
   determining an optimal radio frequency to break the emulsion;
   generating, at a frequency generator, the optimal radio frequency; and
   applying the optimal radio frequency to the emulsion.

17. The method of claim 16, wherein the isolated molecules comprise at least one of asphaltenes and surfactants.

18. The method of claim 16, wherein monitoring the rotations and translations of the one or more of the molecules comprises determining an angular momentum or an mean square displacement of the one or more of the molecules before and after a radio frequency is applied to a simulation cell.

19. The method of claim 16, wherein the radio frequencies applied to the simulation cell are about 500 KHz to about 500 MHz, including about 0.5, 5, 10, 15, 20, 25, 50, 75, 100, 150, 200, 250, 300, 350, 400, 450, or 500 MHz.

20. The method of claim 16, wherein the generated optimal frequency is an electromagnetic energy.

* * * * *